(12) United States Patent
Adamson

(10) Patent No.: US 6,500,930 B2
(45) Date of Patent: Dec. 31, 2002

(54) HEMOGLOBIN-POLYSACCHARIDE CONJUGATES

(75) Inventor: Gordon J. Adamson, Georgetown (CA)

(73) Assignee: Hemosol Inc., Ontario (CA)

( * ) Notice: Subject to any disclaimer, the term of this patent is extended or adjusted under 35 U.S.C. 154(b) by 0 days.

(21) Appl. No.: 09/276,686

(22) Filed: Mar. 26, 1999

(65) Prior Publication Data

US 2002/0040128 A1 Apr. 4, 2002

(51) Int. Cl.[7] ........................................... C07K 14/805
(52) U.S. Cl. ...................................... 530/385
(58) Field of Search ........................................ 530/385

(56) References Cited

U.S. PATENT DOCUMENTS

| | | | | |
|---|---|---|---|---|
| 3,925,344 A | 12/1975 | Mazur | ...................... | 260/112.5 |
| 4,001,200 A | 1/1977 | Bonsen et al. | ............ | 260/112.5 |
| 4,064,118 A | 12/1977 | Wong | ....................... | 260/112.5 |
| 4,857,636 A | 8/1989 | Shia | ........................... | 530/385 |
| 4,900,780 A | 2/1990 | Cerny | ....................... | 525/54.1 |
| 5,250,665 A | 10/1993 | Kluger et al. | ............... | 530/385 |
| 5,439,591 A | 8/1995 | Pliura et al. | ................ | 210/635 |
| 5,529,719 A | 6/1996 | Tye | ............................ | 252/511 |
| 5,532,352 A | 7/1996 | Pliura et al. | ................ | 540/145 |

FOREIGN PATENT DOCUMENTS

| | | |
|---|---|---|
| DE | 2616086 A | 11/1977 |
| EP | 0338916 | 10/1989 |
| FR | 2328478 | 5/1977 |
| FR | 2640141 | 6/1990 |
| WO | WO91/15215 | 10/1991 |

OTHER PUBLICATIONS

Dellacherie et al., Modification of Human Hemoglobin by Covalent Association with Soluble Dextran, Biochemica et Acta, 749 (1983) 106–114.
Bonneaux, et al., Preparation and Oxygen Binding Properties of Soluble Covalent Hemoglobin–Dextran Conjugates, Experimentia 37 (1981).
Database Dissertation Abstracts, University Microfilms International AN =01357490, Bonneaux, Francois: "Role of Aldehydic Dextrans in Developing Covalent Human Hemoglobin Conjugates to be Used as Intravascular Oxygen–Carriers", XP002107868.
Baldwin et al., "Tetrahedron" 37, pp. 1723–1726 (1981) "Synthesis of Polymer–Bound Hemoglobin Samples".
Cerny, L.C. et al., "Mixtures of Erythrocytes and Acellular Fluids: an in Vitro Evaluation", Artif. Cells, Blood Substitutes, Immobilization Biotechnol., 1994, vol. 22, pp. 633–639.
Bonneaux, Francois et al., "Fixation of Various Aldehydic Dextrans Onto Human Hemoglobin: Study of Conjugate Stability", J. Protein Chem., 1995, vol. 14, No. 1, pp. 1–5.
Bonneaux, Francois et al., "Hemoglobin–Dialdehyde Dextran Conjugates:Improvement of Their Oxygen–Binding Properties with Anionic Groups", J. Protein Chem., 1996, vol. 15, No. 5, pp. 461–465.
Klett, D. et al., "Fixation of Aldehydic Dextrans onto Human Deoxyhemoglobin" Biopolymers, 1992, vol. 32, No. 5, pp. 517–522.
Tam, Siu–Cheung et al., "Soluble Dextran–Hemoglobin Complex as a Potential Blood Substitute", Proc. Natl. Acad. Sci. U.S.A., 1976, vol. 73, No. 6 pp. 2128–2131.
Cerny, L.C., et al., "Hydroxyethyl Starch–Hemoglobin Pollymer as a Blood Substitute", Clin. Hemorheol., 1982, vol. 2, No. 4, pp. 355–365.
Wong, J., Tze–Fei et al., "Biophysical Basis of Hypoxic Radioprotection by Deoxygenated Dextran–Hemoglobin" Int. J. Radiat. Oncol., Biol., Phys., 1986, vol. 12, No. 8, p. 1303–1306.
Maout, Etienne et al., "Hydroxyethyl Starch Conjugated to Human Hemoglobin for use in Blood Transfusion:Comparison with Dextran Conjugates", Front, Biomed. Biotechnol., 1993, vol. 1, No. Carbohydrates and Carbohydrate Polymers, pp. 132–140.

Primary Examiner—Karen Cochrane Carlson
(74) Attorney, Agent, or Firm—Nixon & Vanderhye

(57) ABSTRACT

Hemoglobin conjugates useful as a hemoglobin-based oxygen carriers are prepared by reacting hemoglobin with oxidatively ring-opened polysaccharides such as hydroxyethyl starch or dextran, and storing the resultant conjugate under conditions which allow it to transform to a lower molecular weight product, after conjugation. The conjugate is then reductively stabilized to form secondary amino bonds between the hemoglobin and the polysaccharide, and formulated as an BOC.

29 Claims, 7 Drawing Sheets

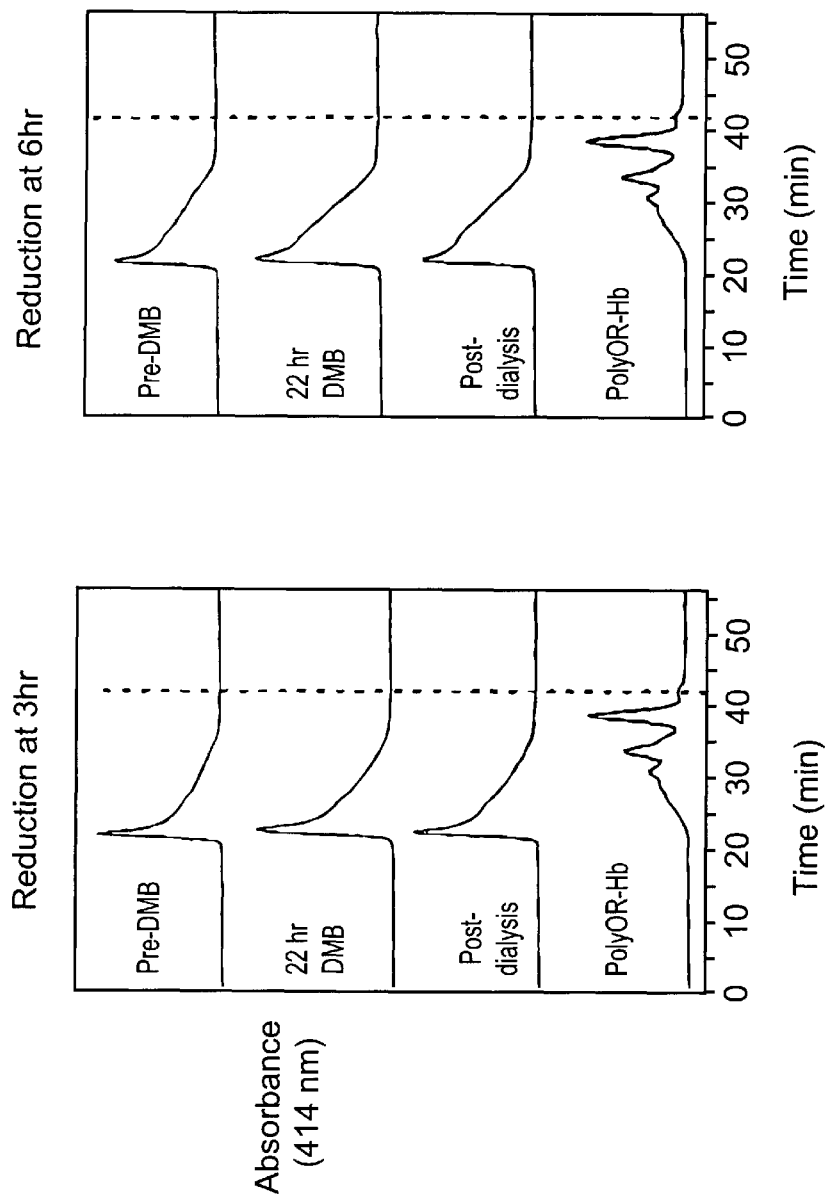

HEMOGLOBIN-POLYSACCHARIDE CONJUGATES

This application claims proity Canadian application 2,233,725, filed Mar. 31, 1998.

FIELD OF THE INVENTION

This invention relates to biocompatible oxygen carriers for administration to patients as a supplement for or a partial replacement for whole blood. More specifically, the invention relates to hemoglobin-based oxygen carriers (HBOCs) for administration to mammals as a blood substitute or supplement, and processes for their preparation.

BACKGROUND OF THE INVENTION

Hemoglobin, as the natural oxygen transporter component of blood, is an obvious candidate to form the basis of a blood substitute, e.g. as an aqueous solution. Extensive scientific work has been done and reported, on attempts to provide a satisfactory hemoglobin solution to act as a blood substitute. The chemical properties of hemoglobin outside the red blood cells are, however, markedly different from its properties inside the red blood cells, e.g. as regards its oxygen affinity. The need for some form of chemical modification of hemoglobin to render it suitable for use as a blood substitute has long been recognized and has been quite extensively investigated.

It is well known that hemoglobin comprises a tetramer of four sub-units, namely two a sub-units each having a globin peptide chain and two β sub-units each having a globin peptide chain. The tetramer has a molecular weight of approximately 64 kilodaltons, and each sub-unit has approximately the same molecular weight. The tetrameric hemoglobin in dilute aqueous solution readily dissociates into α-β dimers and even further under some conditions to α-sub-unit monomers and β-sub-unit monomers. The dimers and monomers have too low a molecular weight for retention in the circulatory system of the body, and are filtered by the kidneys for excretion with the urine. This results in an unacceptably short half life of such a product in the body. The benefit of chemical bonding between the sub-units to ensure the maintenance of the tetrameric form ("intramolecular cross-linking") has previously been recognized. Also, the linking together of two or more tetrameric units to form hemoglobin oligomers and polymers of molecular weight greater than 64 kilodaltons ("intermolecular cross-linking") has also been recognized as desirable in many instances.

Accordingly, one approach to developing HBOCs for clinical use has been intramolecularly cross-linking the hemoglobin units into stabilized tetramers, of molecular weight c. 64 kilodaltons, and optionally oligomerizing these tetramters into oligomers of 2–6 such tetramers, by intermolecular cross-linking. A variety of cross-linking reagents have been proposed for this purpose, including oxidatively ring-opened saccharides such as o-raffinose (U.S. Pat. No. 4,857,636 Hsia and U.S. Pat. No. 5,532,352 Pliura et al., for example), bifunctional imidates such as diethylmalonimidate hydrochloride (U.S. Pat. No. 3,945,344 Muzur), halogenated triazines, divinylsulphones, diisocyanates, glutaraldehyde and other dialdehydes (U.S. Pat. No. 4,001,200 Bonsen et al.), bis-diaspirin esters (U.S. Pat. No. 5,529,719 Tye), bis- and tris-acyl phosphates (U.S. Pat. No. 5,250,665 Kluger et al.) and others Another approach to the preparation of HBOCs with appropriate molecular weight for clinical use has been the coupling of hemoglobin to a biocompatible polysaccharide. Such conjugates would have the advantage as compared with cross-linked and oligomerized hemoglobins of requiring lower quantities of hemoglobin per unit of HBOC, and hence would be more economical to prepare, and have diminished hemoglobin-related toxicities. Conjugation of a colloid to hemoglobin in preparing an HBOC also permits control of fluid properties such as viscosity and colloid osmotic pressure by adjusting the size of the colloid, its degree of modification and the colloid-to-hemoglobin ratio. These same parameters can be used to control :he final molecular weight and vascular retention time of the product.

U.S. Pat. No. 4,064,118 Wong proposes the preparation of a blood substitute or blood extender by chemically coupling hemoglobin with a polysaccharide material selected from dextran and hydroxyethyl starch of molecular weight from about 5 kDa –2,000 kDa. Only the use of dextran is exemplified in this patent, however.

Baldwin et al. "*Tetrahedron*" 37, pp 1723–1726 (1991) "*Synthesis of Polymer-Bound Hemoglobin Samples*" describe the chemical modification of dextran and hydroxyethyl starch (HES) to form aldehyde-substituted polymers, and their subsequent reaction with hemoglobin, to form soluble, polymer-bound hemoglobin. Whilst the products so formed were capable of binding oxygen, they are reported as unsuitable for use as blood substitutes, since their oxygen-binding curves were considerably left-shifted, indicating that they have too high an oxygen affinity ($P_{50}$ too low).

SUMMARY OF THE INVENTION

It is an object of the present invention to provide a novel HBOC.

It is a further object of the invention to provide a novel polysaccharide-hemoglobin conjugate useful as an HBOC.

It is a further object to provide a process for preparing a novel polysaccharide-hemoglobin conjugate useful as an HBOC.

In the process of the present invention, a polysaccharide is used, in oxidatively ring-opened form. In this oxidative form, at least a portion of the saccharide monomeric units are oxidized to present aldehyde groups. The oxidized polysaccharide so formed is then reacted with extracellular hemoglobin, so that the hemoglobin, through primary amine groups of the globin chains reacting with the aldehyde groups of the oxidized polysaccharide, covalently binds to the polysaccharide through Schiff base linkages. Initially and very rapidly there is formed a product which includes species of very high molecular weight, of the order of 500 kDa or higher, in substantial amounts and a wide molecular weight distribution (128→500 kDa).

On maintaining this product under appropriate conditions, in aqueous solution, it can be transformed, to a controlled extent, over a relatively short period of time (e.g 4–48 hours depending upon the conditions) to a much lower molecular weight product (90–200 kDa) with a much narrower molecular weight distribution. This product, after chemical reduction to reduce the Schiff base linkages between the hemoglobin and the polysaccharide to secondary amine bond, turns out to have properties such as oxygen affinity in the range $P_{50}$=4 to 50 mmHg at 37° C., depending on the ligand state of the hemoglobin at the time of conjugation, which makes it eminently suitable as a candidate for a hemoglobin based oxygen carrier for clinical use in mammals. The degree of transformation can be controlled by the timing of the application of the reduction step. Moreover, the resulting product contains no detectable unreacted hemoglobin which, if present, would dissociate to give αβ-dimers suspected of causing renal injury, and no detectable amounts of excessively high molecular weight products (over about 500–600 kDa).

Thus according to the first aspect of the present invention, there is provided a polysaccharide-hemoglobin conjugate useful as a hemoglobin based oxygen carrier and having an oxygen affinity, expressed as partial pressure of oxygen environment required to maintain 50% oxygen saturation, $P_{50}$ of =4–50 mmHg, at 37° C., and containing no detectable residual unbound hemoglobin and no detectable residual amounts of components of molecular weight higher than about 500 kDa, said conjugate having been prepared by reacting hemoglobin with oxidized polysaccharide to form a high molecular weight conjugate complex, and allowing the high molecular weight conjugate complex to degrade by storage in solution at a suitable pH value, readily determinable by simple, routine experiments, and at a temperature from 2° C. to about 45° C. to form said polysaccharide-hemoglobin conjugate.

A further aspect of the invention provides a polysaccharide-hemoglobin conjugate useful as an oxygen transporter, comprising hemoglobin covalently linked through secondary amine linkages from amino groups on the hemoglobin to residues of aldehyde groups on the polysaccharide, said aldehyde groups having been formed by oxidative ring-opening of saccharide monomeric units of the polysaccharide.

According to another aspect, the present invention provides a process of preparing a hemoglobin based oxygen carrier which comprises reacting an oxidatively ring-opened polysaccharide carrying aldehyde groups with hemoglobin to form a Schiff based-linked conjugate thereof, allowing the conjugate to stand under conditions which effect molecular weight reduction of the conjugate, stabilizing the conjugate by reduction of the Schiff base linkages to stable, secondary amine linkages, and recovering a solution of the polysaccharide-hemoglobin conjugate so formed which has no detectable unbound hemoglobin residue and no detectable product residue of molecular weight greater than about 500–600 kDa,

BRIEF REFERENCE TO THE DRAWINGS

FIGS. 10, 11 and 12 are similar sets of chromatograms from products of Example 11 below.

DESCRIPTION OF THE PREFERRED EMBODIMENTS

Figure 2:
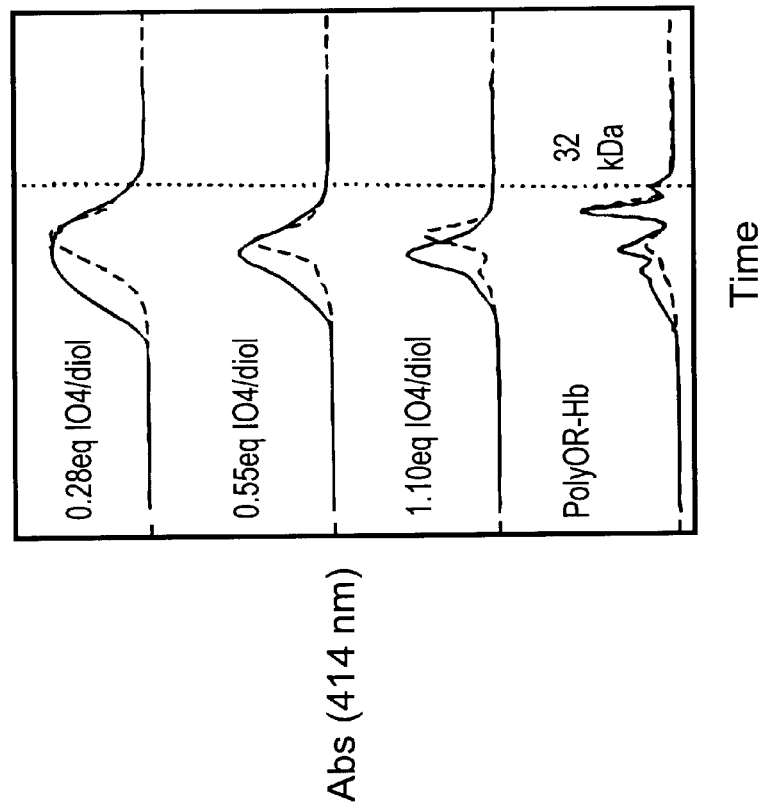
FIGS. 1, 2 and 3 are sets of chromatograms of products of Example 2 below.

Apparent molecular weights described in this application are derived by comparison with size exclusion chromatography elution times of o-raffinose polymerized hemoglobin (polyOR-Hb) standards of known molecular weight. Since hemoglobin-colloid conjugates are suspected to contain significant amounts of trapped water in the extended colloid chain component, the actual molecular weight of the conjugate including only molecules covalently attached to the hemoglobin is less than the apparent molecular weight. However, it is the apparent molecular weight, or excluded volume, that will dictate the in vivo retention time of the conjugate, and so molecular weight as described above will be used to describe the conjugates reported here.

The hemoglobin for use in the process of the present invention is preferably human hemoglobin, derived from red blood cells. However, the invention is applicable also to other types of hemoglobin to form the basis of a blood substitute, such as animal hemoglobins especially bovine hemoglobin, and porcine hemoglobin and the like, and hemoglobin derived from cell culture. Human hemoglobin is currently the preferred choice, to form the basis of a blood substitute for administration to human patients.

The hemoglobin can be recovered and prepared for use in the present invention according to standard, known techniques. Thus, red blood cells are lysed, and cellular debris and stroma are removed therefrom by standard techniques of centrifugation, filtration and the like. Preferably, a solution of hemoglobin with a concentration of 2–20% by weight of hemoglobin is used, to yield a product having the most desirable composition and combination of properties. Final purification can suitably take place chromatographically. The displacement chromatography process described in U.S. Pat. No. 5,439,591 Pliura et al. is beneficially used.

Hemoglobin can naturally exist in the tight (T) conformation as normally assumed by deoxyhemoglobin, or in the relaxed (R) conformation as normally assumed by oxyhemoglobin or carbon monoxyhemoglobin. The oxygen binding characteristics of hemoglobin in the T state are the more desirable characteristics, since the oxygen affinity of hemoglobin in this conformation allows efficient oxygen binding in the lung vasculature and oxygen offloading in the peripheral tissues. It is accordingly preferred to use deoxyhemoglobin in the process of the invention. After conjugation to the hydroxyethyl starch (HES) with or without prior cross-linking, the deoxyhemoglobin retains oxygen binding characteristics of the T-configuration. If, however, one chooses for any reason to start with R-configuration hemoglobin, the preferred process according to the invention stabilizes the hemoglobin into the R-configuration throughout. Mixtures of R- and T-state hemoglobins can be reacted with the HES to obtain products with oxygen binding properties intermediate between those of the R- and T-state configurations.

Deoxygenacion of hemoglobin to form deoxyhemoglobin is preferably conducted by subjecting the hemoglobin solution to treatment with a non-oxygenating gas such as nitrogen, according to known techniques. It is preferred to continue the treatment with a stream of nitrogen, followed by appropriate degassing, for sufficiently long periods of time to effect complete conversion to deoxyhemoglobin in this manner.

Polysaccharides useful in the present invention include those of established biocompatibility, and having saccharide monomeric units capable of oxidative ring opening to form reactive aldehyde groups. They include starches and starch deivativesr dextran, inulin and the like. Preferred among the polysaccharides for use in the present invention are hydroxethyl starch and dextran, with HES being most preferred.

The hemoglobin can be reacted with the oxidized hydroxyethyl starch in its native, non-cross-linked form, or in its cross-linked, 64 kDa tetrameric stabilized form, or in its cross-linked and oligomerized form comprising 64→<500 kDa adducts. When used in its cross-linked form, the preferred cross-linking reagent for preparing cross-linked and cross-linked-oligomerized hemoglobin is a polyaldehyde derived from the oxidative ring-opening of an oligosaccharide such as raffinose (i.e. o-raffinose). A suitable process for preparation of o-raffinose and for its reaction with hemoglobin is described in the above-mentioned U.S. Pat. No. 5,532,352 Pliura et al., the disclosure of which is incorporated herein by reference, Whilst o-raffinose is the preferred cross-linking reagent for use in this embodiment of the invention, it is by no means limited thereto. Any of the other known Hb cross-linking reagents, such as those mentioned previously, for example trimesoylmethyl phosphate (TMMP) described in U.S. Pat. No. 5,250,665 Kluger et al. can be satisfactorily used.

The hydroxyethyl starch starting material for use in preferred embodiments of the present invention suitably has a molecular weight of from about 70 to about 1000 kDa. It is commercially available, in various types and varieties. The type and variety for use in the present invention is not critical. Substantially any of the currently commercially available varieties of HES can be used as the starting material, provided that they have a molecular weight approximately as set out above. Those with a substitution ratio (i.e. number of hydroxyethyl groups to glucose units) of from about 0.5 to 0.7 are particularly suitable.

To prepare the HES for use in the present invention, it is oxidized, so as to create thereon substantial numbers of aldehyde groups. This can be accomplished by a variety of oxidation processes, the preferred one being reaction with a periodate (sodium or potassium). This reaction can take place in aqueous solution at low temperature, e.g. 0–5° C., using an appropriate quantity of sodium periodate, chosen according to the desired degree of oxidation. The reaction is complete in about 1–4 hours. Ultrafiltration or dialysis can be used to remove undesirable low molecular weight salts and HES components, thereby offering a means of controlling the molecular weight range of oxidized HES to be conjugated to the Hb. The oxidized HES can be used directly or is suitably recovered, e.g. by lyophilization, and redissolved in water for conjugation to the hemoglobin.

The conjugation reaction suitably takes place in aqueous solution. The hemoglobin may optionally be cross-linked Hb and/or oligomerized Hb. It may e liganded e.g. with carbon monoxide, (CO-Hb). Lower $P_{50}$ values in the final products are obtained with CO-Hb, higher values with deoxy Hb. Molar ratios of Hb:oxidized HES can range anywhere from about 0.25:1 to 5:1, but are preferably in the 0.5:1–3:1 approximate range. The reaction best takes place at alkaline pH, e.g. in the range 7.5–9.0, and at room temperatures.

The reaction product formed initially, e.g. after about 1 hour is found on analysis to have a very high molecular weight, with components of molecular weight well in excess of 500 kDa, no matter what the molecular weight of the starting polysaccharide may have been. This initial product also contains a broad range of molecular weight products. One can effect a controlled reduction in the molecular weight of the product, to a product containing no components of molecular weight higher than about 500,000, and to a product of narrow molecular weight distribution (e.g containing predominantly species of 100–200 kDa molecular weight), by maintaining the product in aqueous solution, preferably in the approximate pH range 7.2–10, and at or close to room temperature (15° C.–30° C.), for a period of time up to about 48 hours. There is very little, if any, residual 32 kDa species. The amount of 32 kDa species is so small that no special steps for its removal are necessary.

The conjugate so formed must be stabilized by reducing the (reversible) Schiff base linkages between the Hb and the HES to stable secondary amine linkages and by reducing any unreacted aldehyde groups. The reduction can be accomplished in a single stage, in which the Schiff base linkages and the aldehyde groups are reduced in a single stage, or in two separate stages. Powerful reducing agents will be effective in one stage, less powerful reducing agents requiring a two-stage process.

This step of reduction is preferably used as the means of control of the molecular weight and molecular weight distribution of the final product, by appropriate timing thereof. Once the reduction has been completed, the product is stabilized and no further changes in molecular weight or molecular weight distribution of any significance will occur on storage. Accordingly, analysis of samples of reaction product at intervals allows timing of the reduction step to stabilize the product at the chosen characteristics.

Borane dimethylamine is the preferred choice as the reducing agent. This is powerful enough to accomplish both reduction reactions in a single stage. Other water soluble borane lower alkyl amine reducing agents including but not limited to borane-tert-butylamine, borane-ammonia; borane-dimethylamine; borane-trimethylamine; borane triethylamine; and pyridine borane can also be used. Other useful reducing agents are sodium cyanoborohydride and sodium borohydride.

Reduction of the Schiff bases formed during the conjugation, and reduction of any residual unreacted aldehyde groups, most suitably takes place in aqueous solution at a temperature range of 2–25° C., for a period of time from 10–36 hours, preferably 24 hours. The reaction mixture is suitably buffered to pH 7–10, preferably to 8.0–9.5. The molar ratio of reducing agent to the sum of imine and aldehyde groups is in the range 1:1 to 5:1, preferably 1.5:1 to 3.5:1 based on the stoichiometry of reducing agent to aldehyde groups added to initiate cross-linking.

It is preferred to use a final step of diafiltration, to remove residual low molecular weight products such as starch degradation residues, dimethylamino borane residues, salts, buffer residues, etc. Then the product can be mixed with a suitable excipient, to form an HBOC.

The conjugate so prepared exhibits eminently suitable properties for use as the basis of an HBOC. It exhibits low oxygen affinity ($P_{50}$=20–50 mmHg) along with a narrow molecular weight distribution of product (MWD 100–200 kDa), with no detectable product of m. wt. 32 kDa under conditions which promote dissociation to $\alpha\beta$-dimers, or m. wt. above about 500 kDa.

For storage prior to use, it is suitable to remove all oxygen from the product to prevent autoxidation. Deoxygenated product can be stored under conditions which prevent introduction of oxygen, either frozen or at higher temperatures. Oxygen can be introduced prior to administration, or the product can be allowed to acquire oxygen in vivo. The carbonmonoxy form can be stored in a similar manner and oxygenated prior to use. The product can be stored frozen in the oxygenated form, or at higher temperatures until the degree of autoxidation is deemed unacceptable.

The invention is further described for illustrative purposes only, in the following specific, non-limiting examples.

EXAMPLE 1

Preparation of Oxidized Hydroxyethyl Starch 9.0 g hydroxyethyl starch with weight average molecular weight (MW) of 450 kDa, having a degree of hydroxyethyl substitution of 0.7, was dissolved in 90 mL water. 0.49, 0.98 and 1.96 g sodium meta-periodate, representing approximately 0.3, 0.6 and 1.2 eq, respectively, of periodate per mol of vicinal diol present in the HES, were added to separate 30 mL aliquots of this solution. These amounts are sufficient to provide approximately 30%, 60% and 100% oxidation of available diol groups. After 4 hours reaction in the dark at 4° C., the solutions were dialyzed extensively against chilled water using a 15 kDa molecular weight cutoff membrane. Final retentates were lyophilized to white powders and stored at room temperature. Alternatively, the dialyzed oxidized HES solution could be used directly for conjugation of Hb. HES with MW of 200 kDa and substitution of 0.5 was oxidized and prepared in a similar manner. Oxidized HES was also prepared by direct oxidation of HES formulated in 0.9% NaCl. Measurements of periodate consumption and final aldehyde content indicated that the range or periodate used resulted in partial to complete oxidation of all available diol groups, and that the degree of oxidation was readily controlled by varying the amount of periodate used.

EXAMPLE 2

Prepration of Conjugates with Various Oxidized HES and CO-Hemoglobin

Figure 1:
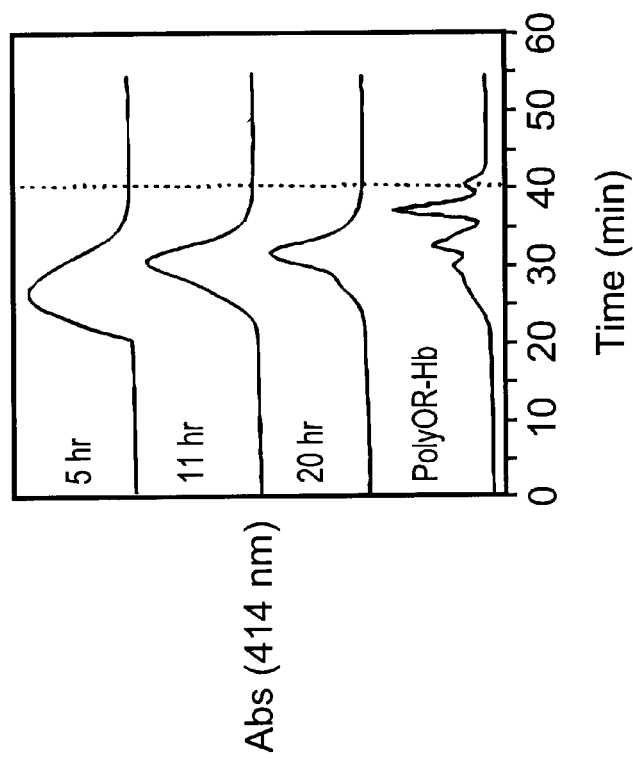

The reaction of CO-Hb with various relative ratios of oxidized HES (HES-CHO) was studied. Periodate equivalents for oxidation were calculated based on the expected vicinal diol content of the HES. In one case, 0.54 g oxidized 450 kDa HES, prepared using 1.2 eq periodate as described in example 1, was dissolved in 3.0 mL 100 mM HEPES buffer pH 8.1. This HES-CHO solution was added to carbonmonoxylated hemoglobin (COHb, 200 mg/mL in water) in the following ratios: 0.76 mL HES-CHO:0.041 mL COHb, 0.73:0.078, and 0.61:0.195, giving final Hb concentrations of approximately 10, 20 and 50 mg/mL, respectively. The reactions were allowed to proceed at 22–25° C., at pH 8, and samples were withdrawn at various times for MW determination using a Pharmacia Superdex 200 column (1×30 cm) eluted with 0.5 M $MgCl_2$+25 mM Tris pH 7.2 at 0.4 mL/min. At all three HES:COHb ratios, Hb was completely modified in the first several hours to give species having elution times comparable to polyHb controls with MW greater than 128 kDa and ranging to above the exclusion limit of the column (>500 kDa polyhb). FIG. 1 of the accompanying drawings shows the chromatogram derived from the 0.5:1 Hb:HES product (50 mg Hb/ml), taken at various times and compared with (bottom curve) the poly Hb control. The dashed vertical line represents the elution time of 32 kDa unmodified $\alpha$-$\beta$ dimer. The absorbance at 414 nm characteristic of hemoglobin is tracked in the eluting fractions. During the next 30 hours, the elution times of the product decreased to give species having elution times comparable to polyHb controls with MW of 128 kDa, with no unmodified Hb detectable and no species above the exclusion limit of the column. The pattern of MW evolution and final product MW ranges were similar at all three HES:Hb ratios, as with HES oxidized with 0.6 eq periodate. Conjugates prepared using HES oxidized with 0.3 eq periodate per diol typically contained significant material co-eluting with unmodified a-b dimer. Higher levels of oxidation were therefore preferable for generating conjugate free of unmodified dimer.

The average MW of conjugates formed during the first several hours was lower when less Hb was used. Similar reactions and results were obtained using oxidized 200 kDa HES as described in Example 1. Average MW of final products were higher when 450 kDa HES was used in comparison to 200 kDa HES. FIG. 2 of the accompanying drawings shows chromatograms of the final products of Hb+HES-CHO for HES 200/0.5 (broken lines) and HES 450/0.7 (solid lines), at different degrees of oxidation as indicated, all at 1:1 Hb:HES-CHO ratios.

Hb-HES conjugates obtained using periodate oxidized 70 kDa HES (0.3, 0.6 and 1.2 eq. periodate vs. calculated diol) also formed higher MW species during the early phase of conjugation, followed by transformation to lower MW (FIG. 3), Average SW of early phase conjugates, as well as the time required to convert to lower MW species, was dependent on the degree of oxidation of the HES 70. After 48 hours conjugation, some material coeluting with the 32 kDa unmodified Hb component of the polyOR-Hb control remained in the conjugate derived from the lowest degree of HES oxidation (0.3 eq periodate per calculated diol). Significant material eluting at the analytical column exclusion limit remained after 48 hour in the reaction using the most highly oxidized HES 70 (1.2 eq periodate per calculated diol). Product free of unmodified hemoglobin and material eluting at the column exclusion limit was obtained within 48 hours of reaction with HES oxidized by 0.6 eq. periodate per calculated diol.

EXAMPLE 3

Simultaneous Large Scale Preparation of High and Low MW Hb-HES Conjugates

Two Hb-HES conjugates of different MW were prepared from a single reaction, in which a portion of the early conjugation product having high MW was isolated and stabilized, allowing the remaining conjugation product to undergo transformation to a lower MW product before stabilization. A comparison of physical and in vivo properties of the two products was made so that the beneficial properties of one over the other could be demonstrated.

944 g HES (200 kDa, degree of substitution=0.5) was dissolved in 8 L WFI, cooled to 4° C., then 370 g $NaIO_4$ added and the mixture stirred in the dark for 5.3 hours. All $NaIO_4$ dissolved in less than 1 hour. The mixture was filtered (0.2 um) then diafiltered against 12 volumes room temperature WFI (water for injection) using a 30 kDa regenerated cellulose membrane. It was then deoxygenated by contact with $N_2$ through a hollow fibre membrane. Lyophilized samples indicated a final concentration of 128 mg HES-CHO/mL. 1.2 L of COHb (23.2 g/dL in WFI) was combined with 2.0 L 200 mH HEPES pH 8.1 buffer, then oxygenated and deoxygenated by contact with $O_2$ then $N_2$ through a hollow fibre membrane. 4.5 kg of the HES-CHO solution (128 g/L) was combined with the deoxygenated Hb (3.2 L at 9.0 g/dL) and the mixture maintained under deoxy conditions. The MWD of the conjugates forming was monitored by size exclusion chromatography.

Figure 4:
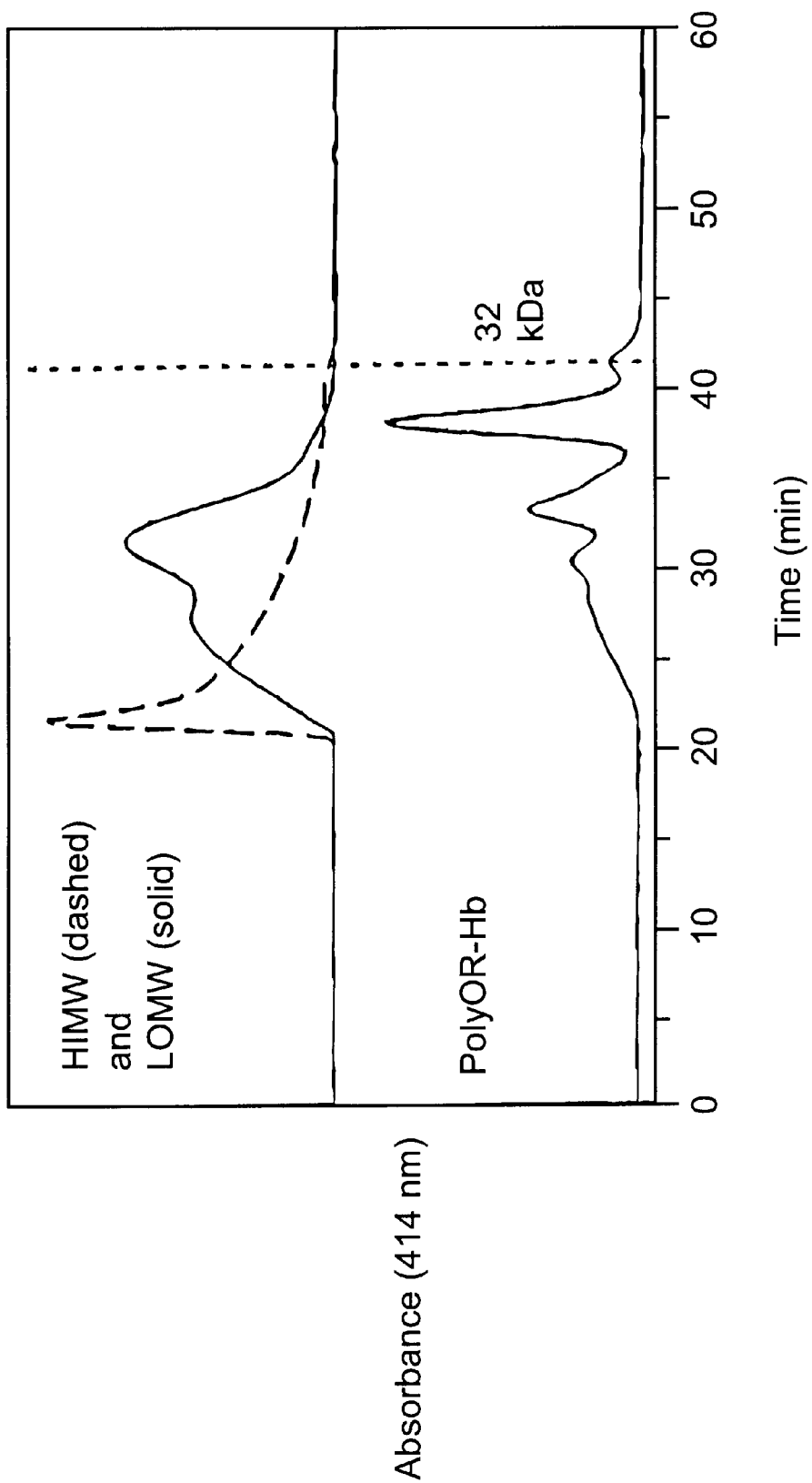
FIG. 4 is a size exclusion chromatographic analysis of products of Example 3 below.

After 3 hours conjugation, half of the reaction volume was transferred under N2 to a separate vessel and 56 mL 3 M NaOAc and 196 g DMB, dissolved in 1.7 L WFI, were added. The final DMB initial aldehyde ratio was 1.5:1. The mixture was kept under N2 at ambient temperature for 23 hours before CO charging and diafiltration. At 29 hours after initiation of the Hb-HES conjugation reaction, the other half of the mixture was treated similarly with NaOAc and DMB for 17.5 hours. Both DMB-reduced reactions were then CO charged and diafiltered vs. WFI then Ringer's lactate (approximately 10 volumes for each solution). The pH was adjusted to 7.5–7.6 with 0.1 N HCl. Both solutions were concentrated such that colloid osmotic pressure was 80–100 mm Hg. Products were oxygenated and approximately three-quarters removed for sterile filtration and packaging in the oxy form. The remaining amounts of each were deoxygenated and packaged in the deoxy form. Oxygenated products were stored at −80° C., deoxygenated products at 4° C. The higher MW product, obtained by reduction of early stage conjugation product, is hereafter referred to as HIMW HES-Hb. The lower MW product, obtained by reduction o the late stage conjugation product, is hereafter referred to as LOMW HES-Hb. MW distributions assessed by size exclusion chromatography are shown in FIG. 4. MW distribution did not change over four months storage at either 4 or −80° C.

The colloid osmotic pressure (COP) of HIMW HES-Hb was consistently higher than LOMW HES-Hb at the various concentrations tested for both products (Table 1). Viscosities were 86.9 and 3.0 cSt at 6.5 and 9.0 g Hb/dL for HIMW HES-Hb and LOMW HES-Hb, respectively. HIMW HES-Hb, which is comparable in MW distribution to HES- and dextran-Hb conjugates prepared by others, therefore has colloidal properties which would be expected to result in a greater change in blood fluid and rhoeological properties than LOMW HES-Hb. The deleterious effects of higher MW HES plasma components on rheological factors such as viscosity and erythrocyte aggregation, and on blood clotting, have been described (Treib et al., Thrombosis and Haemostasis 74:1452–6 (1995)).

TABLE 1

Concentration dependence of COP for HIMW and LOMW HES-Hb

| HIMW HES-Hb | | LOMW HES-Hb | |
|---|---|---|---|
| Conc (g Hb/dL) | COP (mm Hg) | Conc (g Hb/dL) | COP (mm Hg) |
| 6.5 | 103.5 | 9.0 | 85.4 |
| 4.2 | 35.7 | 6.1 | 36.6 |
| 2.1 | 8.6 | 3.1 | 11.3 |

EXAMPLE 4

Effect of Ligand State on Final $P_{50}$

COHb (55 mg/mL in water) was oxygenated and deoxygenated by exposure to oxygen then nitrogen, respectively. 200 kDa HES was oxidized using 0.6 eq periodate as described in Example 1, and made up to 60 mg/mL in 100 mM HEPES pH 8.1, and degassed and purged with nitrogen. 2.5 mL of this oxidized HES solution was added to 0.8 mL of the deoxygenated Hb solution, providing 1 eq Hb per mol of initial unoxidized 200 kDa HES. After 48 hours at 22–25° C. under nitrogen, the reaction mixture was made 0.3 M in sodium acetate, then 3 eq dimethylamine borane per mole of initial aldehyde were added. After 24 hours, the solution was charged with CO gas, and exhaustively dialyzed against lactated Ringer's solution. A similar procedure was conducted in which COHb, without removal of the CO ligand, was reacted with 200 kDa HES oxidized by 0.6 eq periodate. Oxygen binding properties were measured for both products using a Hemox-Analyzer (TCS Instruments, Southhampton, Pa., U.S.A,) at 37° C. Conjugation of deoxygenated Hb resulted in a final $P_{50}$ of 26 mm Hg. Conjugation of COHb resulted in a final $P_{50}$ of 4 mm Hg. Both products were non-cooperative.

EXAMPLE 5

Use of Cross-Linked Hemoglobin 200 kDa HES was oxidized by 0.3 eq and 0.6 eq periodate in separate reactions as described in Example 1, and made up to 125 mg/mL in 270 mM sodium bicarbonate pH 8.1. 3.0 mL of each oxidized HES solution was added to separate 1.0 mL aliquots of trimesoyl tris(methyl phosphate)(TMMP)-cross-linked Hb (64 kDa cross-linked Hb, U.S. Pat. No. 5,250,665 Kluger et al., 125 mg/mL in water), and likewise to 1.0 mL aliquots of o-raffinose polymerized Hb (64-<500 kDa Hb polymers, U.S. Pat. No. 5,532,352 Pliura et al., 117 mg/mL), for a total of four reactions, in all cases providing 1 eq Hb per mol of initial unoxidized 200 kDa HES. Both hemoglobin products were in the CO form. After 30 hours reaction at 22–25° C. under CO gas, sodium acetate was added to a final concentration of 0.3 M. 3 eq dimethylamine borane per mol of initial aldehyde was then added. After 24 hours, the reactions were dialyzed (10 kDa MWCO) against water then lactated Ringer's solution at pH 7.4. Oxygen binding properties were then recorded using a Hemox-Analyzer at 37° C.

MW distributions of all Hbs were shifted to higher values. With Hb and TMMP-cross-linked-Hb, it was possible to modify all starting Hb and there was no detectable void volume material (Superose 12, dissociating conditions) within 48 hr. PolyOR-Hb conjugates contained significant void volume material. $P_{50}S$ (37°) were: HES+CO–TM-Hb, 5–7 mmHg; HES+CO-polyOR-Hb, 5–7 mmHg. All products were non-cooperative.

EXAMPLE 6

Variation in Reaction Time and Temperature

The effect of shorter reaction times and lower temperature (12 vs. 22° C.) on Hb-HES MWD was studied on a small scale. Oxidized forms of 200 kDa and 450 kDa HES were used.

Figure 5:
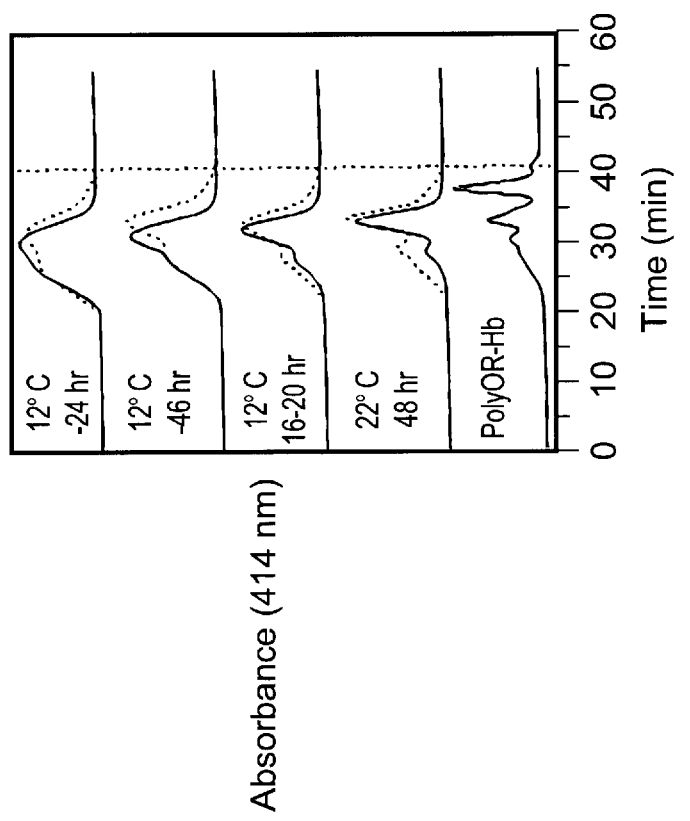
FIG. 5 is a similar set of chromatograms of products of Example 6 below.

Deoxygenated Hb was used. COHb (50 mg/mL in 75 mM HEPES buffer pH 8.1) was oxygenated and deoxygenated by exposure to oxygen then nitrogen, respectively. Oxidized HES, derived from either 200 or 450 kDa HES using 0.6 or 1.2 eq periodate per mol of vicinal diol, respectively, was dissolved in 100 mM HEPES buffer pH 8.1 to a final concentration of 60 mg/mL, and the solutions were then degassed and purged with nitrogen. 0.253 mL of Hb was combined with 1.6 mL of oxidized 200 kDa HES solution, and 0.498 mL of Hb was combined with 1. mL of oxidized 450 kDa HES solution, in both cases providing 1 eq Hb per mol of initial unoxidized 200 kDa or 450 kDa HES. These solutions were allowed to react at 22° C. under nitrogen, and identical solutions were prepared and allowed to react at 12° C. MWD were determined at various time points as described in Example 2. Chromatographic profiles are shown in FIG. 5.

Final MWD was narrower at 22° C. for both oxidized HES's, and at longer reaction times for both temperatures. Average MW of the 450 kDa HES product (solid lines) was greater than for the 200 kDa derivative (dashed lines), with the MW difference being larger at the lower temperature. Reactions proceeded more slowly at lower temperature, resulting in greater average MW and wider molecular weight range compared to similar reaction times at higher temperature.

EXAMPLE 7

Scale-Up

Conjugation of oxidized HES to deoxy Hb was scaled up for in vivo evaluation.

Figure 6:
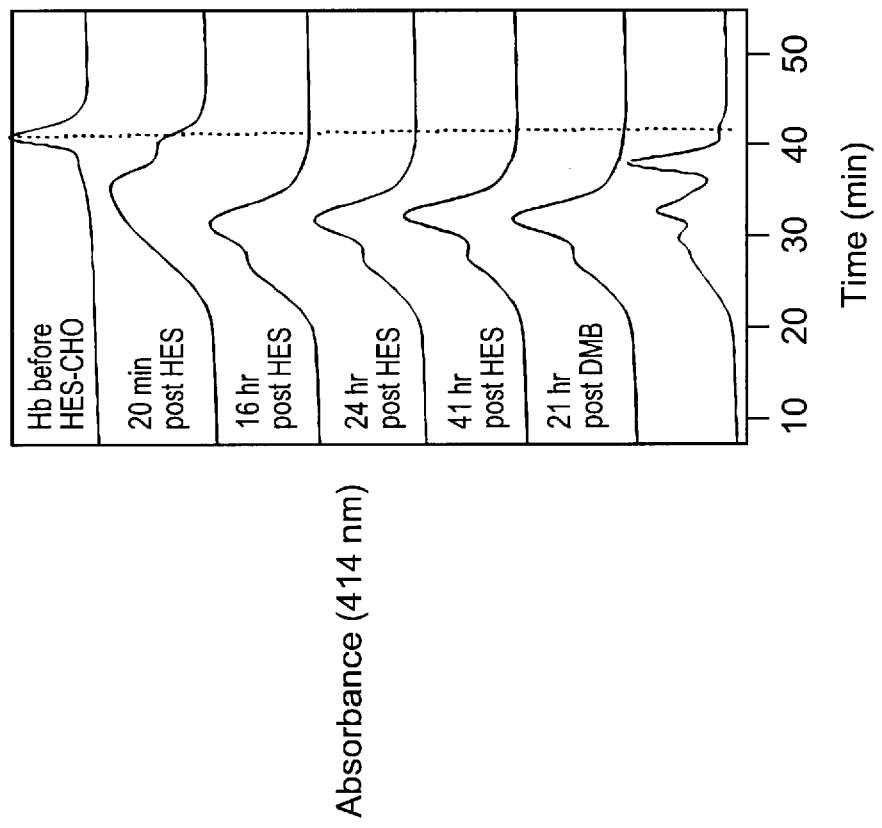
FIG. 6 is a similar set of chromatograms of products of Example 7 below.

COHb was made up to 125 mg/mL in 100 mM HEPES buffer pH 8.1 and rendered ligand-free by contact with oxygen then nitrogen using a hollow fibre gas exchanger. 47 g of oxidized 200 kDa HES, prepared as in Example 1 using 0.6 eq periodate, was dissolved in 280 mL 100 Ma HEPES buffer pH 8.1, then degassed and purged with nitrogen. The oxidized HES solution was then added to the deoxyHb and maintained under nitrogen at 22–25° C. with periodic measurement of MWD. Within 16 hours, all Hb was modified and no product aluted at the exclusion limit of the column (FIG. 6). The lowermost curve, presented for comparison purposes, is derived from Hb cross-linked with oxidatively ring-opened raffinose (polyOR-Rb) The reaction was made 0.4 M in sodium acetate, and 36 g dimethylamine borane was added, representing approximately 3 eq borane per mole of initial aldehyde. After 21 hours, the reaction mixture was oxygenated, diafiltered (10 kDa MWCO) against lactated Ringer's solution and adjusted to pH 7.4. The product had a $P_{50}$ (37° C.)=26 mmHg and was non-cooperative. Low angle laser light scattering analysis of size exclusion chromatographic effluent indicated a MW of 90–210 kDa. No free aldehyde was detectable.

Analysis of in vivo halflife shows that the Hb-HES product is retained for extensive periods. A volume of the product, adjusted to 3.0 g Hb/dL in lactated Ringer's solution, equivalent to 10% of total blood volume was infused into conscious rats and the vascular retention time determined. The half-life was 6.0 hours, compared to 5.1 hours determined for an equivalent volume of polyOR-Hb, adjusted to 10.0 g/dL in lactated Ringer's solution.

EXAMPLE 8

Conjugation of Hb with oxidized dextran and transformation to lower MW

Figure 3:
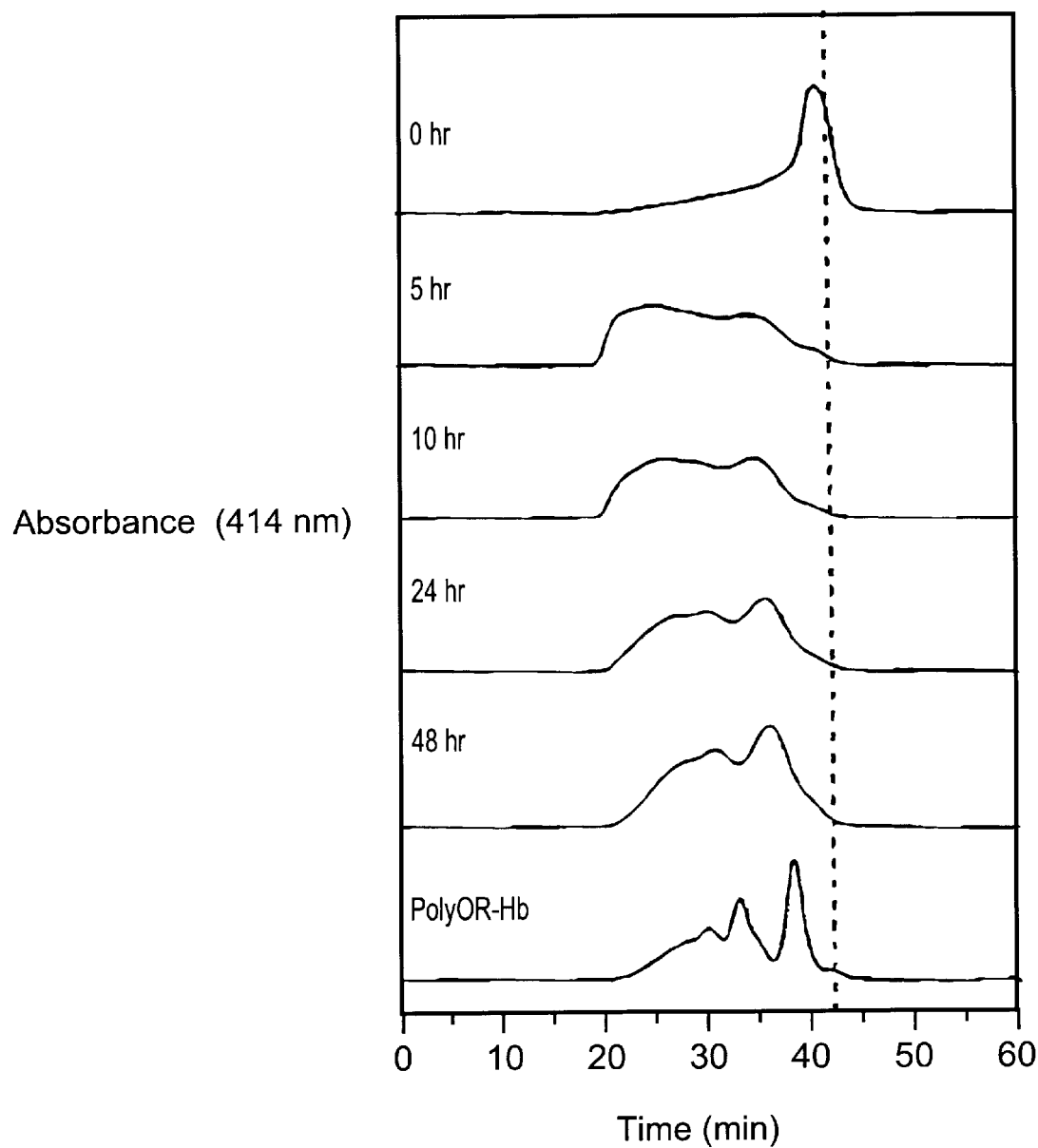
Figure 7:
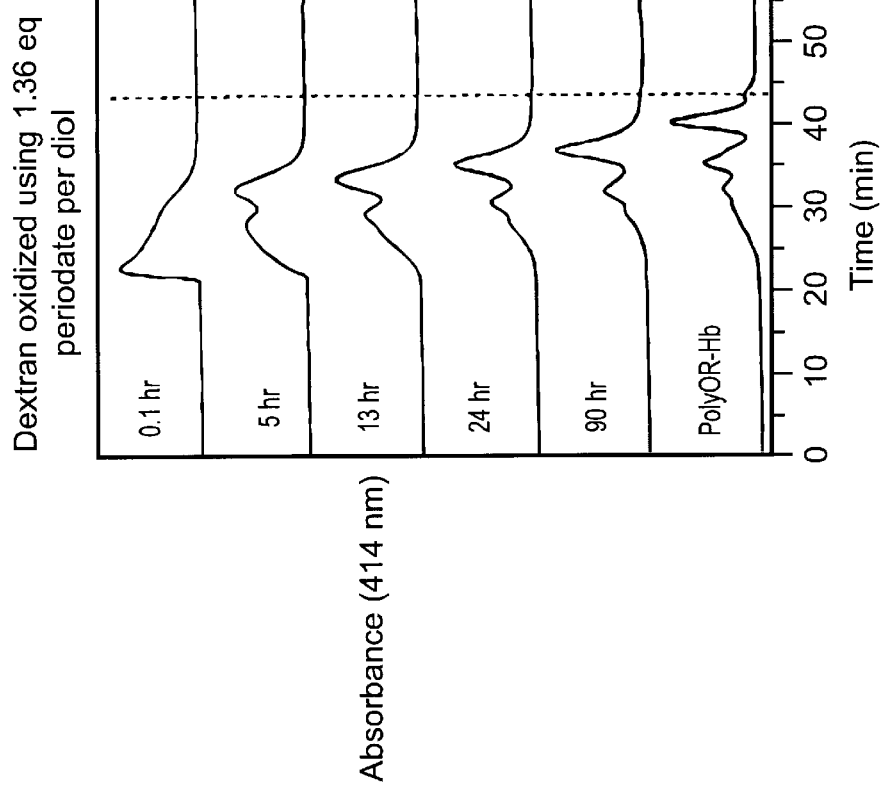
FIGS. 7 and 8 are similar sets of chromatograms of products of Example 8 below.
Figure 8:
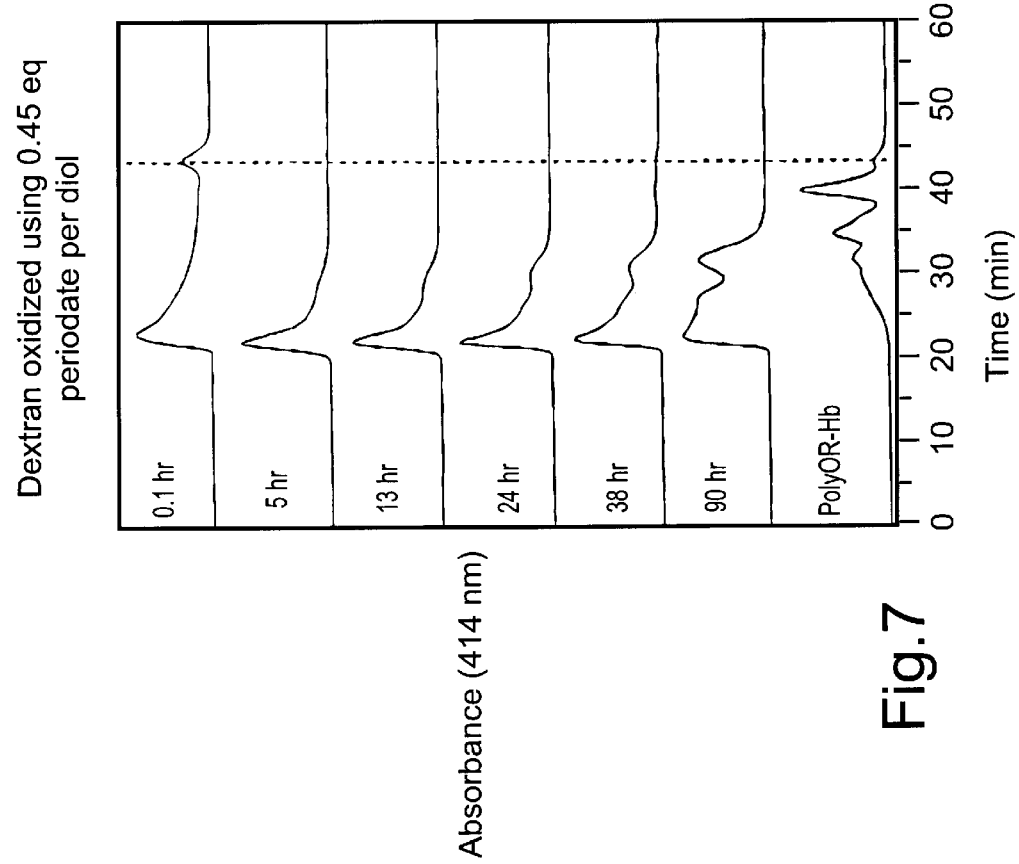

Two oxidized dextrans were prepared using either 0.45 or 1.36 eq periodate per diol (2 diols per dextran chain monomer). Solutions of 2.0 g dextran (260 kDa) dissolved in 40 mL 4° C. water were treated with either 2.39 or 7.18 g sodium periodate (0.45 and 1.36 eq, respectively). After 4 hours stirring in the dark at 4° C., the solutions were dialyzed (10 kDa MW cutoff) and lyophilized to white powders. 50 mg of oxidized dextran in 1 mL 80 mM HEPES pH 8.1 buffer was combined with 0.062 mL COHb (200 mg/mL) and the conjugation reaction was monitored by size exclusion chromatography under dissociating, non-denaturing conditions (0.5 M $MgCl_2$+25 mM Tris pH 7.4). The results are shown on FIG. 7, for the product where dextran was oxidized using 0.45 equivalents of periodate per diol, and on FIG. 8 for the 1.36 equivalents periodate per diol experiment. Both reactions showed initial formation of high MW species eluting largely in the column exclusion volume. Conjugate derived from the highly oxidized dextran was more rapidly transformed to low MW species than when using less oxidized dextran. The similarity in MW profiles for the polyOR-Hb control and the highly oxidized dextran conjugate, with the exception of overall higher MW for the latter, suggests the conjugate is made up of polymerized, cross-linked Hb species which are decorated with polysaccharide fragments. This configuration is also suggested for oxidized HES conjugates obtained under some conditions (FIG. 3).

EXAMPLE 9

Plasma Half-life of LOMW and HIMW Hb-HES Conjugates

Male Sprague Dawley rats were acclimatized for one week with free access to food and tap water. On the day of the experiment, rats were anesthetized with Ketaset (ketamin hydrochloride, 60 mg/kg, i.m.) and Atravet (acepromazine maleate, 2.0 mg/kg, i.m.). The right femoral artery and vein were cannulated using a 2.5–3.5 cm PE10 tubing connected to a PE50 tubing filled with heparin-saline solution (50 USP units heparin/mL). Two to 3.5 cm of PE10 were inserted into the lower abdominal aorta via the femoral artery and vena cava via the femoral vein. Both cannulas were tunneled subcutaneously to the nape and exteriorized. At the end of the surgery the surgical site was losed using surgical thread. Both cannulas were filled with heparin-saline solution (500 USP unit/mL) at the end of the procedure. Animals were then outfitted with a rodent tethering harness and miniature feed-through swivels and placed individually in metabolic cages. Animals were allowed to recover from the surgery 0.5 to 1.5 hours and resided in the metabolic cage throughout the entire experiment. After the recovery period, the venous cannula was connected to an automatic infusion pump. Conscious animals were subjected to infusion of the control solutions (10 g/dL polyOR-Hb in lactated Ringer's solution, and the same diluted to 4 g/dL in plasma) or test articles (the products of Example 2, low molecular weight (LOMW) and high molecular weight (HIMW) HES-Hb, 5.0 and 3.5 g Hb/dL in lactated Ringer's solution), respectively equivalent to 10% of total blood volume, delivered at 0.2 mL/min. Blood samples were collected 20 min after the end of infusion (time=0.33 hr post-infusion) and at time=1, 3, 6, 10, 22, 28 and 34 hours. Plasma was separated by centrifugation and stored at −80° C. until analyzed by size exclusion chromatography. Total hemoglobin was calculated from background-corrected absorbances recorded at 414 nm, and plotted against time of blood collection, and plasma half-lives were derived from single exponential fits. Plasma half-lives were 5.1, 5.5, 8.9 and 15.6 hours for the 4 and 10 g/dL polyOR-Hb, and the LOMW and HIMW RES-Hb solutions, respectively.

When compared with the half-life obtained for the product of Example 7, which had a similar molecular weight distribution to that of LOMW, it appears from the limited experimental data that a longer half-life is obtained for the latter product which is derived from the more highly oxidized HES.

EXAMPLE 10

In Vitro Stability of Hb-HES in Plasma

Figure 9:
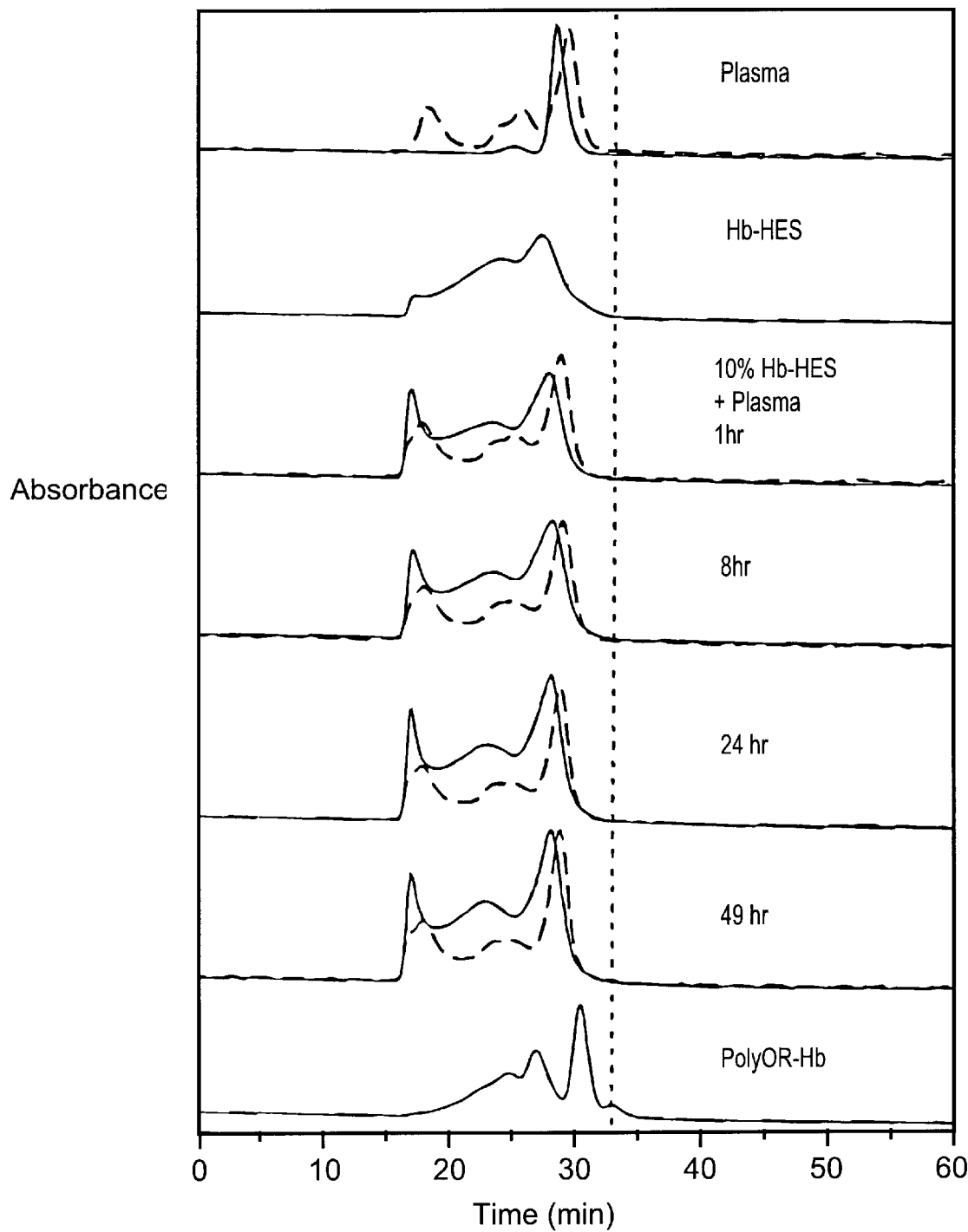
FIG. 9 is a similar set of chromatograms illustrating the results of Example 10 below.

Hb-HES prepared in Exammle 6 was diluted 10-fold in rat plasma and incubated at 37° C., simulating a 5–10% (vol/vol) topload administration. The mixture was analyzed by size exclusion chromatography under dissociating, non-denaturing conditions (0.5 M $MgCl_2$+25 mM Tris pH 7.4), over a 49 hour period. The results are shown on FIG. 9. No low molecular weight species, indicative of product degradation, were detected during this time. High molecular weight species, eluting at the exclusion limit of the analytical column, appeared within the first hour of incubation. These species correspond to high molecular weight complexes of the modified hemoglobins and rat haptoglobin, in agreement with observations made using several other polymerized hemoglobin products incubated in plasma.

EXAMPLE 11

Stabilization of Various MW Species During Hb-HES Conjugation

Dimethylamine borane (DMS) reduction was used to terminate molecular weight changes occurring during conjugation of Hb to oxidized HES. 2.0 mL COHb (200 mg/mL in H2o) combined with 490 uL 80 mM HEPES pH 8.1 was deoxygenated. 674 mg $N_2$ charged oxidized HES (prepared previously from RES 450/0.7, 1.10 eq periodate per calculated diol) was dissolved in 6.8 mL of degassed 80 mM HEPES pH 8.1. 950 uL of the Hb solution was added to the oxidized HES solution, giving a final Hb:HES(450 kDa) ratio of 1:1. After 3 hours, 2 mL of this reaction mixture were added to a freshly prepared solution of 152 mg $N_2$-charged DMB (providing approximately 3 eq DEB per initial aldehyde calculated for the oxidized HES), dissolved in 1.6 mL degassed water with 350 uL 4 M NaOAc added. A 2 mL aliquot of the Hb-HES reaction was similarly treated after 6 hours. After 22 hours, the reactions were charged with co and dialyzed extensively vs. water over 72 hours at 4° C. MW distributions during conjugation, reduction and after dialysis were measured by size exclusion chromatography under dissociating, non-denaturing conditions (0.5 M MgCl2 +25 mM Tris pH 7.4). The results are shown on FIG. 10, for the products subject to reduction at 3 hours, FIG. 11 for the products subject to reduction at 6 hours, and FIG. 12 for the non-reduced products. The MW distribution of products observed at 3 hours and 6 hours (both high MW conjugates) did not change significantly during 22 hours of reduction at room temperature, nor during 72 hours dialysis at 4° C. Therefore, reduction with 3 eq. DMB per initial aldehyde prevented transformation of the Hb-BES conjugate to lower MW, as seen in samples which were not reduced (FIG. 10). Stabilization of high MW species was also seen when using fewer equivalents of DMB per initial Ialdehyde, as described in Example 3. This reduction method can be used to stabilize any MW distribution that develops during the conjugation reaction.

What is claimed is:

1. A process for preparing a reduced hemoglobin-polysaccharide conjugate composition comprising:
    (a) subjecting a starting polysaccharide to oxidative ring-opening to produce an oxidatively ring-opened polysaccharide carrying aldehyde groups;
    (b) reacting said oxidatively ring-opened polysaccharide with a hemoglobin under conditions suitable to form schiff base linkages between the hemoglobin and the ring-opened polysaccharide to form an initial hemoglobin-polysaccharide conjugate composition;
    (c) degrading the oxidatively ring-opened polysaccharide by maintaining the conjugate composition under controlled conditions of aqueous solution with predetermined pH for a period of time until a desired lower average molecular weight hemoglobin-polysaccharide composition as compared to the initial hemoglobin-polysaccharide composition is reached to form a detectably degraded further hemoglobin-polysaccharide conjugate composition with a lowered average molecular weight, a lowered amount of unreacted hemoglobin species and narrowed molecular weight distribution as compared to said initial hemoglobin-polysaccharide conjugate composition; and
    (e) recovering said reduced hemoglobin-polysaccharide conjugate composition.

2. A process as claimed in claim 1 wherein there is no detectable unmodified hemoglobin and no conjugate of molecular weight greater than about 500–600 kDa in said reduced hemoglobin-polysaccharide conjugate composition.

3. The process of claim 1 wherein the starting polysaccharide has a molecular weight of at least 70 kDa.

4. The process of claim 3 wherein the starting polysaccharide has a molecular weight of between 70–1000 kDa.

5. The process of claim 4 wherein the starting polysaccharide has a molecular weight of between 70–450 kDa.

6. The process of claim 5 wherein the starting polysaccharide has a molecular weight of between 70–260 kDa.

7. The process of claim 6 wherein the starting polysaccharide has a molecular weight of 70 kDa.

8. The process of claim 1 wherein the starting polysaccharide is dextran or hydrosyethyl starch.

9. The process of claim 8 wherein the starting polysaccharide is hydroxyethyl starch.

10. The process of claim 1 wherein the initial conjugate is maintained in step (c) in aqueous solution at a pH of from about 7.2–10, at a temperature of from 15–30 degrees Celsius to decrease the average molecular weight and narrow the molecular weight distribution of the initial conjugate composition.

11. The process of claim 10 wherein the initial conjugate is maintained in aqueous solution for 4–48 hours.

12. The process of claim 11 wherein the molecular weight of the conjugates in the resulting composition is predominantly between about 90–200kDa.

13. The process of claim 1 wherein said reducing step (d) is a single stage of reduction to effect Schiff base reduction and substantially simultaneously to reduce aldehyde groups.

14. The process of claim 13 wherein the reduction is effected with a boron-based reducing agent.

15. The process of claim 1 wherein said reducing step (d) is carried out in two successive stages of reduction, first to effect Schiff base reduction and second to reduce aldehyde groups.

16. The process of claim 1 wherein the hemoglobin is human hemoglobin.

17. The process of claim 16 wherein the hemoglobin is deoxyhemoglobin.

18. The process of claim 17 wherein the heoglobin is intramolecularly and/or intermolecularly cross-linked.

19. A reduced hemoglobin-polysaccharide conjugate composition produced by the process of claim 1.

20. A reduced hemoglobin-polysaccharide composition produced by the process of claim 9.

21. A reduced hemoglobin-polysaccharide conjugate composition comprising alkaline degraded oxidatively ring-opened polysaccharide.

22. The reduced hemoglobin-polysaccharide conjugate composition of claim 21 produced using hydroxyethyl starch or dextran as a starting polysaccharide.

23. The reduced hemoglobin-polysaccharide conjugate composition of claim 22 wherein the starting polysaccharide is hydroxyethyl starch.

24. The reduced hemoglobin-polysaccharide conjugate composition of claim 23 wherein the hemoglobin is human hemoglobin.

25. The reduced hemoglobin-polysaccharide conjugate composition of claim 24 wherein the hemoglobin is deoxyhemoglobin.

26. The reduced hemoglobin-polysaccharide conjugate composition of claim 24 wherein the hemoglobin is intramolecularly and/or intermolecularly cross-linked.

27. The reduced hemoglobin-polysaccharide conjugate composition of claim 24 wherein the starting polysaccharide is hydroxyethyl starch having a molecular weight from about 70 to about 1000 kDa.

28. The reduced hemoglobin-polysaccharide conjugate composition of claim 27 wherein the hydroxyethyl starch has a substitution ratio from about 0.5 to 0.7.

29. The reduced hemoglobin-polysaccharide conjugate composition of claim 28 having a P50 from 5–50 at 37 degrees Celsius.

* * * * *